United States Patent
Nakata et al.

(10) Patent No.: US 11,684,752 B2
(45) Date of Patent: Jun. 27, 2023

(54) ACTUATOR, ACTUATOR MODULE, ENDOSCOPE, ENDOSCOPE MODULE, AND CONTROLLING METHOD

(71) Applicant: SONY CORPORATION, Tokyo (JP)

(72) Inventors: Akihiro Nakata, Kanagawa (JP); Satoshi Nakamaru, Kanagawa (JP); Hiroichi Ishikawa, Tokyo (JP); Kazuhito Wakana, Kanagawa (JP); Yoshio Goto, Kanagawa (JP)

(73) Assignee: Sony Corporation, Tokyo (JP)

( * ) Notice: Subject to any disclaimer, the term of this patent is extended or adjusted under 35 U.S.C. 154(b) by 1050 days.

(21) Appl. No.: 16/322,289

(22) PCT Filed: Aug. 3, 2017

(86) PCT No.: PCT/JP2017/028164
§ 371 (c)(1),
(2) Date: Jan. 31, 2019

(87) PCT Pub. No.: WO2018/030250
PCT Pub. Date: Feb. 15, 2018

(65) Prior Publication Data
US 2019/0192821 A1   Jun. 27, 2019

(30) Foreign Application Priority Data
Aug. 8, 2016 (JP) .............. JP2016-155631

(51) Int. Cl.
*A61B 1/008* (2006.01)
*A61M 25/01* (2006.01)
(Continued)

(52) U.S. Cl.
CPC ........... *A61M 25/0155* (2013.01); *A61B 1/00* (2013.01); *A61B 1/0053* (2013.01);
(Continued)

(58) Field of Classification Search
CPC .................. A61B 1/00; A61B 1/00119; A61B 1/005–009; B25J 9/14; G02B 23/24;
(Continued)

(56) References Cited

U.S. PATENT DOCUMENTS 5,179,934 A * 1/1993 Nagayoshi ......... A61B 1/00183
600/152
2003/0065250 A1* 4/2003 Chiel ..................... A61B 34/72
600/115
(Continued)

FOREIGN PATENT DOCUMENTS

| JP | H09-79204 | 3/1997 |
|---|---|---|
| JP | 2006-520180 | 8/2006 |
| JP | 2006-311630 | 11/2006 |

OTHER PUBLICATIONS

International Search Report prepared by the Japan Patent Office dated Oct. 12, 2017, for International Application No. PCT/JP2017/028164.

*Primary Examiner* — Levi Gannon
(74) *Attorney, Agent, or Firm* — Sheridan Ross PC

(57) ABSTRACT

An actuator is provided with a tubular actuator element and a supporting body which supports an inner peripheral surface of the actuator element. An internal pressure of the actuator element is higher than an external pressure of the actuator element.

17 Claims, 16 Drawing Sheets

(51) Int. Cl.
*A61B 1/005* (2006.01)
*H02N 11/00* (2006.01)
*G02B 23/24* (2006.01)
*A61B 1/00* (2006.01)
*H02N 1/00* (2006.01)
*B25J 9/10* (2006.01)
*B25J 9/14* (2006.01)

(52) U.S. Cl.
CPC .......... *A61B 1/0056* (2013.01); *A61B 1/0057* (2013.01); *G02B 23/24* (2013.01); *H02N 1/006* (2013.01); *H02N 11/00* (2013.01); *A61B 1/008* (2013.01); *B25J 9/1075* (2013.01); *B25J 9/14* (2013.01)

(58) Field of Classification Search
CPC .......... H02N 1/006; H02N 2/00; H02N 2/005; H02N 2/006; H02N 2/0075; H02N 2/02; H02N 2/04; H02N 11/00
See application file for complete search history.

(56) References Cited

U.S. PATENT DOCUMENTS

| | | | |
|---|---|---|---|
| 2004/0217671 A1 | 11/2004 | Rosenthal et al. | |
| 2006/0238065 A1 | 10/2006 | Ishibashi et al. | |
| 2008/0022517 A1 | 1/2008 | Rosenthal et al. | |
| 2010/0286479 A1* | 11/2010 | Ashida | A61M 25/10184 600/116 |
| 2011/0105846 A1* | 5/2011 | Yoshie | F04B 9/103 600/156 |
| 2013/0085336 A1* | 4/2013 | Kasai | A61B 1/0053 600/149 |
| 2014/0090724 A1* | 4/2014 | Mevius | F16K 31/165 137/488 |
| 2016/0249900 A1* | 9/2016 | Aoki | A61B 18/1492 606/130 |
| 2017/0112358 A1* | 4/2017 | Aoki | A61B 1/00042 |
| 2018/0014826 A1* | 1/2018 | Scheib | A61B 17/07207 |
| 2019/0226937 A1* | 7/2019 | Glime, III | F15B 13/024 |
| 2019/0257984 A1* | 8/2019 | She | G02C 7/049 |

* cited by examiner

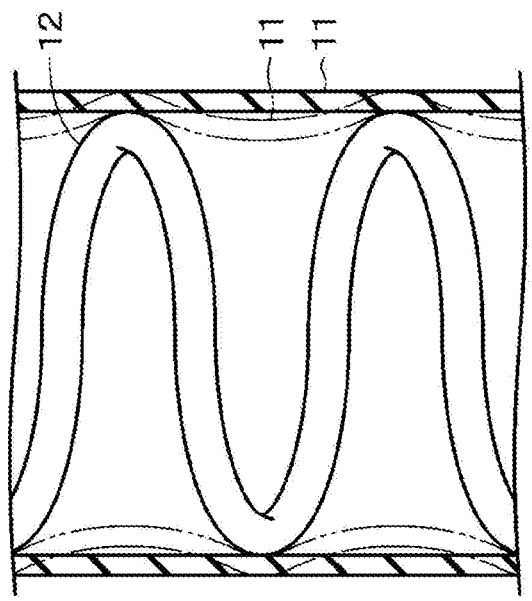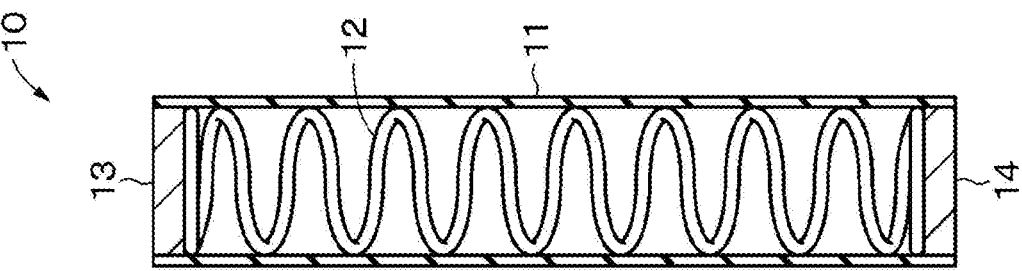

ACTUATOR, ACTUATOR MODULE, ENDOSCOPE, ENDOSCOPE MODULE, AND CONTROLLING METHOD

CROSS REFERENCE TO RELATED APPLICATIONS

This application is a national stage application under 35 U.S.C. 371 and claims the benefit of PCT Application No. PCT/JP2017/028164 having an international filing date of 3 Aug. 2017, which designated the United States, which PCT application claimed the benefit of Japanese Patent Application No. 2016-155631 filed 8 Aug. 2016, the entire disclosures of each of which are incorporated herein by reference.

TECHNICAL FIELD

The present technology relates to an actuator, an actuator module, an endoscope, an endoscope module, and a controlling method.

BACKGROUND ART

An actuator which winds a tensioned dielectric elastomer soft actuator around a spring and expand and contract or bend to be deformed by application of a voltage is suggested (refer to, for example, Patent Document 1). This actuator is characterized in generating large displacement having a small size and a light weight.

CITATION LIST

Patent Document

Patent Document 1: Japanese Unexamined Patent Application Publication No. 2006-520180

SUMMARY OF THE INVENTION

Problems to be Solved by the Invention

However, the actuator described above might cause insulation breakdown.

An object of the present technology is to provide an actuator, an actuator module, an endoscope, an endoscope module, and a controlling method capable of improving insulation resistance.

Solutions to Problems

In order to solve the above problem, a first technology is an actuator provided with a tubular actuator element, and a supporting body which supports an inner peripheral surface of the actuator element, in which an internal pressure of the actuator element is higher than an external pressure of the actuator element.

A second technology is an endoscope provided with the actuator of the first technology.

A third technology is an actuator module provided with an actuator including a tubular actuator element, and a supporting body which supports an inner peripheral surface of the actuator element, a control unit which controls drive of the actuator, and a pressurizing unit which pressurizes an internal space of the actuator.

A fourth technology is an endoscope module provided with the actuator module of the third technology.

A fifth technology is an actuator provided with an actuator element, and a supporting body which supports the actuator element, in which an internal pressure of the actuator element is higher than an external pressure of the actuator element.

A sixth technology is a controlling method provided with detecting a pressure in an internal space of an actuator, and pressurizing the internal space of the actuator on the basis of a result of the detection.

Effects of the Invention

According to the present technology, insulation resistance of the actuator may be improved.

BRIEF DESCRIPTION OF DRAWINGS

FIG. 1A is a cross-sectional view illustrating a configuration of an actuator according to a first embodiment of the present technology. FIG. 1B is an enlarged view illustrating a part of FIG. 1A.

FIG. 13 is a flowchart for illustrating a method of controlling an internal pressure at power on.

MODE FOR CARRYING OUT THE INVENTION

Figure 2A:
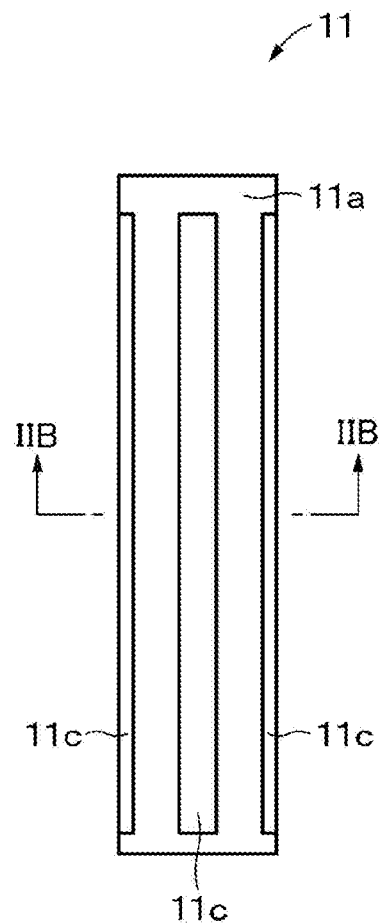
FIG. 2A is a side view illustrating a configuration of an actuator element.

The embodiments of the present technology are described in the following order.

1 First Embodiment (Example of Actuator)
2 Second Embodiment (Example of Endoscope Module)
3 Third Embodiment (Example of Endoscope Module)
4 Fourth Embodiment (Example of Actuator)
5 Fifth Embodiment (Example of Actuator)

1 First Embodiment

[Summary]

In order to figure out a cause of occurrence of insulation breakdown, the inventors of the present invention performed finite element method (FEM) analysis regarding an actuator provided with a tubular actuator element and a coil spring (supporting body) which supports an inner peripheral surface of the actuator element. As a result, the following was found. In other words, in the actuator having the above-described configuration, the actuator element covering a side surface of the coil spring bites into a space between the coil spring and a constriction might occur on the side surface of the actuator element. When such constriction occurs, a thickness of the actuator element becomes nonuniform, and the insulation breakdown tends to occur at a portion where the thickness is small.

Therefore, the inventors of the present invention conducted intensive studies to suppress the constriction occurring on the side surface of the actuator element. As a result, a configuration in which an internal pressure of the actuator is made higher than an external pressure of the actuator was found. Hereinafter, the actuator having such a configuration is described.

[Configuration of Actuator]

An actuator 10 according to a first embodiment of the present technology is a so-called electrostrictive actuator, and is provided with a cylindrical actuator element 11, a cylindrical coil spring 12 which supports an inner peripheral surface of the actuator element 11, and sealing members 13 and 14 which close openings at both ends of the actuator element 11 as illustrated in FIG. 1A. The actuator 10 may further be provided with a cylindrical protective layer not illustrated which covers an outer peripheral surface of the actuator element 11.

The actuator 10 is suitably used in a medical instrument such as an endoscope, an industrial instrument, an electronic device, a speaker, an artificial muscle, a robot, a robot suit and the like. The actuator 10 may be continuously usable or disposable. In a case where the actuator 10 is applied to the medical instrument such as the endoscope, it is preferable that the actuator 10 is disposable from a hygienic viewpoint.

The actuator 10 includes a sealed cylindrical internal space and the coil spring 12 is provided in the internal space. The internal space is filled with gas as a fluid. The gas is at least one type of air, a rare gas, carbon dioxide and the like, for example. An internal pressure of the actuator 10 is higher than an external pressure of the actuator 10. For this reason, it is possible to suppress occurrence of constriction as indicated by a dashed-two dotted line in FIG. 1B on the peripheral surface of the actuator element 11, so that insulation resistance of the actuator 10 may be improved. In this specification, the pressure in the internal space of the actuator 10 is referred to as the internal pressure of the actuator 10, and the pressure of the external space of the actuator element 11 is referred to as the external pressure of the actuator 10.

Hereinafter, the actuator element 11, the coil spring 12, the sealing members 13 and 14, and the protective layer included in the actuator 10 are sequentially described.

(Actuator Element)

The actuator element 11 has a sheet shape. The actuator element 11 may be formed into a cylindrical shape in advance, or may be wound around the coil spring 12 to have the cylindrical shape.

Figure 2B:
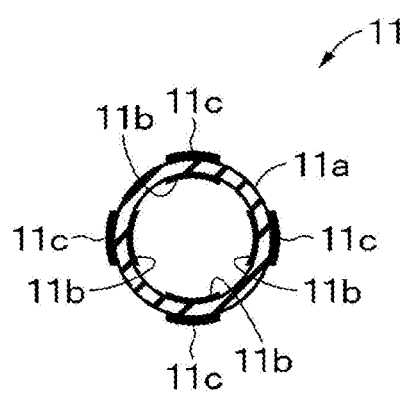
FIG. 2B is a cross-sectional view taken along line IIB-IIB of FIG. 2A.

The actuator element 11 is a so-called dielectric elastomer actuator element and is provided with, as illustrated in FIGS. 2A and 2B, a cylindrical dielectric layer 11a, a plurality of electrodes (first electrodes) 11b provided on an inner peripheral surface of the dielectric layer 11a, and a plurality of electrodes (second electrodes) 11c provided on an outer peripheral surface of the dielectric layer 11a. The electrode 11b may be directly formed on the inner peripheral surface of the dielectric layer 11a or may be bonded via a bonding layer. Furthermore, the electrode 11c may be directly formed on the outer peripheral surface of the dielectric layer 11a or may be bonded via a bonding layer. Herein, an adhesive layer is defined as one type of the bonding layer.

(Dielectric Layer)

The dielectric layer 11e is a sheet having a stretching property. The dielectric layer 11a includes, for example, an insulating elastomer as an insulating stretching material. The dielectric layer 11a may contain an additive as necessary. As the additive, for example, one or more types of a crosslinking agent, a plasticizer, an antioxidant, a surfactant, a viscosity adjusting agent, a reinforcing agent, a coloring agent and the like may be used. As the insulating elastomer, for example, an elastomer containing one or more types of acrylic rubber, silicone rubber, ethylene-propylene-diene terpolymer (EPDM), natural rubber (NR), butyl rubber (IIR), isoprene rubber (IR), acrylonitrile-butadiene copolymer rubber (NBR), hydrogenated-acrylonitrile-butadiene copolymer rubber (H-NBR), hydrin rubber, chloroprene rubber (CR), fluororubber, urethane rubber, and the like may be used. Pre-strain may be applied to the dielectric layer 11e.

(Electrode)

The electrodes 11b and 11c are opposed to each other with the dielectric layer 11a interposed therebetween and extend in a height direction of the actuator element 11. A plurality of electrodes 11b and a plurality of electrodes 11c are arranged at regular intervals in a circumferential direction of the dielectric layer 11a. FIGS. 2A and 2B illustrate an example in which four electrodes 11b and four electrodes 11c are arranged at regular intervals in the circumferential direction of the dielectric layer 11a. A wire not illustrated is connected to the electrodes 11b and 11c, and voltage is applied between the electrodes 11b and 11c opposed to each other with the dielectric layer 11a interposed therebetween.

The electrodes 11b and 11c are thin films having a stretching property. Since the electrodes 11b and 11c have the stretching property, the electrodes 11b and 11c may be deformed following deformation of the dielectric layer 11a. The electrodes 11b and 11c may be any of thin films produced by either a dry process or a wet process. The electrodes 11b and 11c include a conductive material and a binder (binding agent) as necessary. The electrodes 11b and 11c may further include an additive as necessary.

The conductive material may also be a conductive particle. A shape of the conductive particle may be, for example, a spherical shape, an ellipsoidal shape, a needle shape, a plate shape, a scale shape, a tubular shape, a wire shape, a bar shape (rod shape), an irregularly shape, and the like, but the shape is not especially limited thereto. Note that two or more types of particles having the above-described shape may be used in combination.

As the conductive material, one or more types of metal, a metal oxide, a carbon material, and a conductive polymer may be used. Here, it is defined that the metal includes semi metal. The metal includes metal such as copper, silver, gold, platinum, palladium, nickel, tin, cobalt, rhodium, iridium, steel, ruthenium, osmium, manganese, molybdenum, tungsten, niobium, tantalum, titanium, bismuth, antimony, and lead, an alloy thereof or the like, for example; however, the metal is not limited thereto. The metal oxide includes an indium tin oxide (ITO), a zinc oxide, an indium oxide, an antimony-added tin oxide, a fluorine-added tin oxide, an aluminum-added zinc oxide, a gallium-added zinc oxide, a silicon-added zinc oxide, a zinc oxide-tin oxide system, an indium oxide-tin oxide system, a zinc oxide-indium oxide-magnesium oxide system and the like, for example; however, the metal oxide is not limited thereto.

The carbon material includes carbon black, porous carbon, carbon fiber, fullerene, graphene, a carbon nanotube, a carbon micro coil, nanohorn and the like, for example; however, the material is not limited thereto. As the conductive polymer, for example, a conductive polymer such as a linear conjugated system, an aromatic conjugated system, a mixed conjugated system, a heterocyclic conjugated system, a hetero atom-containing conjugated system, a double stranded conjugated system, or a two-dimensional conjugated system; however, the polymer is not limited thereto.

As the binder, it is preferable to use at least one type of an elastomer, a gel, and oil. This is because the stretching property may be imparted to the electrodes 11b and 11c. As the elastomer, for example, one or more types of silicone-based, acrylic-based, urethane-based, and styrene-based elastomers and the like may be used. As the additive, for example, one or more types of a crosslinking agent, a plasticizer, an antioxidant, a surfactant, a viscosity adjusting agent, a reinforcing agent, a coloring agent and the like may be used.

The electrodes 11b and 11c may include a composite material of the conductive polymer and a block copolymer. Specific examples of the composite material include a composite material of polyaniline and styrene-ethylene butylene-styrene (SEBS) copolymer. Furthermore, the electrodes 11b and 11c may contain a polymer gel material and an electrolyte. As a specific example of a combination of these materials, there may be a combination of a polyacrylamide gel and a LiF aqueous solution.

(Coil Spring)

The coil spring 12 is an example of a supporting body which may be curved in an arbitrary direction and elastically deformed. The coil spring 12 is a coil-shaped spring obtained by winding a linear member such as a metal wire into a cylindrical spiral shape, and a space is formed between the linear member. Therefore, the coil spring 12 supports the inner peripheral surface of the actuator element 11 discretely in the height direction of the actuator element 11. By thus supporting the inner peripheral surface of the actuator element 11, the actuator element 11 is easily deformed, and the actuator 10 may easily perform expanding operation and bending operation. Here, "the inner peripheral surface of the actuator element 11 is supported discretely in the height direction of the actuator element 11" means that the inner peripheral surface of the actuator element 11 is supported at separated positions in the height direction of the actuator element 11. Here, intervals between the separated positions may be constant or may be changed.

(Sealing Member)

The sealing members 13 and 14 have a disk shape. The sealing members 13 and 14 include metal or a polymer material. The sealing members 13 and 14 may include an elastomer and the like and elastically deformable. The sealing members 13 and 14 may be a device (for example, an electronic device such as a camera) provided at an end of the actuator 10 or an operating unit of the actuator 10.

(Protective Layer)

The protective layer is for protecting the electrode 11c and is a sheet having a stretching property. The protective layer contains a polymer resin having an insulating property. As the polymer resin, for example, vinyl chloride may be used. In the actuator 10 according to the first embodiment, the occurrence of the constriction in the actuator element 11 is suppressed, so that entry of air between the outer peripheral surface and the protective layer of the actuator element 11 may be suppressed.

[Operation of Actuator]

An example of the operation of the actuator 10 according to the first embodiment of the present technology is described below.

When drive voltage is applied between the electrodes 11b and 11c opposed to each other with the dielectric layer 11a interposed therebetween, an attractive force due to the Coulomb force is applied to both the electrodes 11b and 11c. Therefore, the dielectric layer 11a arranged between the electrodes 11b and 11c is pressed in a thickness direction thereof to become thin and stretched.

On the other hand, when the drive voltage applied between the electrodes 11b and 11c opposed to each other with the dielectric layer 11a interposed therebetween is canceled, no attractive force due to the Coulomb force acts on the electrodes 11b and 11c. Therefore, due to a restoring force of the dielectric layer 11a, the dielectric layer 11a has its original thickness and contracts to return to its original size.

In a case where the drive voltage is applied to one set of electrodes 11b and 11c out of a plurality of sets of electrodes 11b and 11c opposed to each other with the dielectric layer 11a interposed therebetween, the actuator 10 bends by the stretch of the dielectric layer 11a arranged between the electrodes 11b and 11c. When the drive voltage applied to one set of electrodes 11b and 11c is canceled, the actuator 10 returns to its original cylindrical shape.

[Method of Manufacturing Actuator]

Next, a method of manufacturing the actuator 10 is described. First, a rectangular actuator element 11 is wound around a peripheral surface of the coil spring 12 to form a tubular shape, or the coil spring 12 is inserted into the actuator element 11 formed in advance in the tubular shape. The constriction occurs on the peripheral surface of the actuator element 11 after the winding or insertion.

Next, one opening of the actuator element 11 is closed by fitting the sealing member 13 into one opening of the actuator element 11 and the like. Next, the other opening of the actuator element 11 is closed by fitting the sealing member 14 into the other opening of the actuator element 11 and the like. As a result, the actuator 10 having the sealed internal space is obtained. Next, a gas injection means such as a syringe is stuck into one of the sealing members 13 and 14, gas injected into the internal space of the actuator 10 to increase the internal pressure of the actuator 10 to higher than the external pressure, and thereafter the gas injection means is pulled out. As a result, the actuator 10 illustrated in FIG. 1A in which the constriction on the peripheral surface of the actuator element 11 is suppressed may be obtained.

[Effect]

In the actuator 10 according to the first embodiment, since the internal pressure of the actuator 10 is higher than the external pressure, the occurrence of the constriction on the actuator element 11 may be suppressed (refer to FIG. 1B). This makes it possible to suppress nonuniformity of the thickness of the actuator element 11. Therefore, the insulation resistance of the actuator 10 may be improved.

Furthermore, by suppressing the constriction of the actuator element 11, the following effect is also obtained.

A deformation amount (bending amount) per electric field strength of the actuator 10 may be improved.

A side surface of the actuator 10 becomes smoother, so that the side surface of the actuator 10 is less likely to be caught by the surroundings during use. Therefore, in a case where the actuator 10 is applied to the endoscope, operability of the endoscope is improved such that the endoscope is easily inserted into a human body or the like.

In a case where surface treatment by spray coating and the like is applied to the side surface of the actuator element 11, the surface treatment may be performed more uniformly.

Since the constriction of the actuator element 11 may be suppressed without adding a part having a weight, the above-described effect may be obtained without deteriorating bendability of the actuator 10.

[Variation]
(Variation of Supporting Body)

Although the configuration of using the coil spring 12 as the supporting body is described in the first embodiment, the supporting body is not limited to the coil spring 12, and the supporting body may be used as long as this may support the inner peripheral surface of the actuator element 11 discretely in the height direction of the actuator element 11. An example of the supporting body other than the coil spring 12 is hereinafter described.

Figure 3:
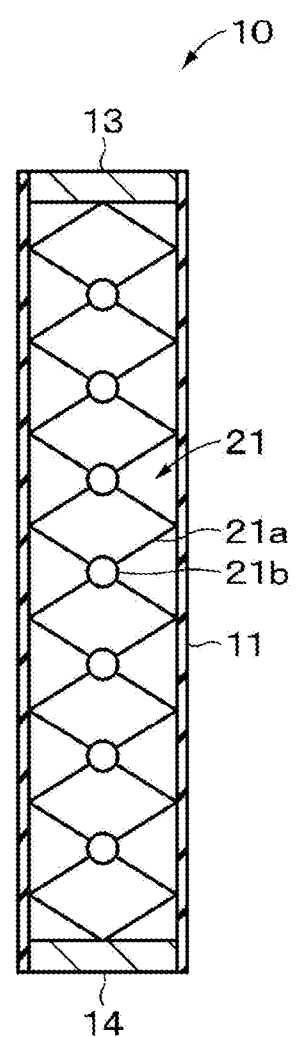
FIG. 3 is a cross-sectional view illustrating a variation of a supporting body.

As illustrated in FIG. 3, the actuator 10 may be provided with a connected body 21 including a plurality of supporting units 21a and a plurality of joint mechanisms 21b in place of the coil spring 12. The plurality of supporting units 21a supports the inner peripheral surface of the actuator element 11 discretely in the height direction of the actuator element 11. The joint mechanism 21b has, for example, a spherical shape and connects adjacent supporting units 21a so as to be rotatable in an arbitrary direction. Note that the joint mechanism 21b may be a part of the supporting unit 21a.

Figure 4B:
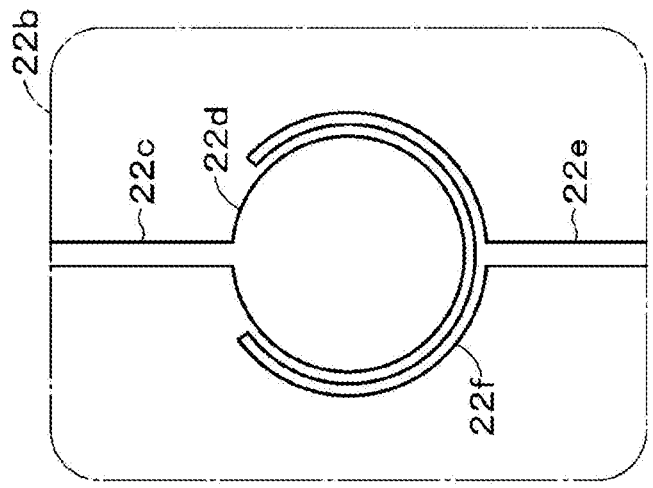
FIG. 4B is an enlarged view illustrating a part of FIG. 4A.
Figure 4A:
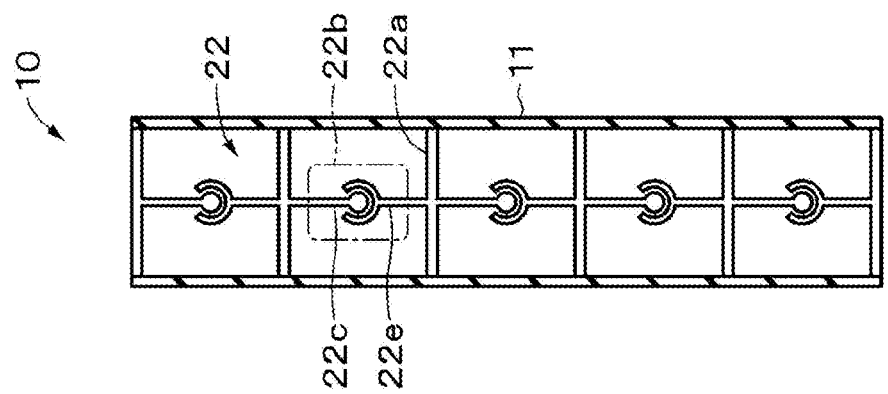
FIG. 4A is a cross-sectional view illustrating a variation of a supporting body.

As illustrated in FIGS. 4A and 4B, the actuator 10 may be provided with a connected body 22 including a plurality of disk-shaped supporting units 22a and a plurality of ball joint mechanisms 22b in place of the coil spring 12. The plurality of ball joint mechanisms 22b connects adjacent supporting units 22a so as to be rotatable in an arbitrary direction. The plurality of supporting units 22a is provided so as to be spaced apart from each other by a predetermined distance and supports the inner peripheral surface of the actuator element 11 discretely in the height direction of the actuator element 11. A shaft portion 22c is perpendicularly erected at the center of one surface of the supporting unit 22a, and a spherical portion (so-called ball stud) 22d is provided at a tip end thereof. On the other hand, a shaft portion 22e is perpendicularly erected at the center of the other surface of the supporting unit 22a, and a socket 22f which is in spherical contact with the spherical portion 22d is provided at a tip end thereof. The socket 22f is in spherical contact with the spherical portion 22d to support the spherical portion 22d so as to be rotatable in an arbitrary direction. The spherical portion 22d and the socket 22f form the ball joint mechanism 22b. The openings at both ends of the actuator element 11 are closed by the supporting units 22a.

Figure 5B:
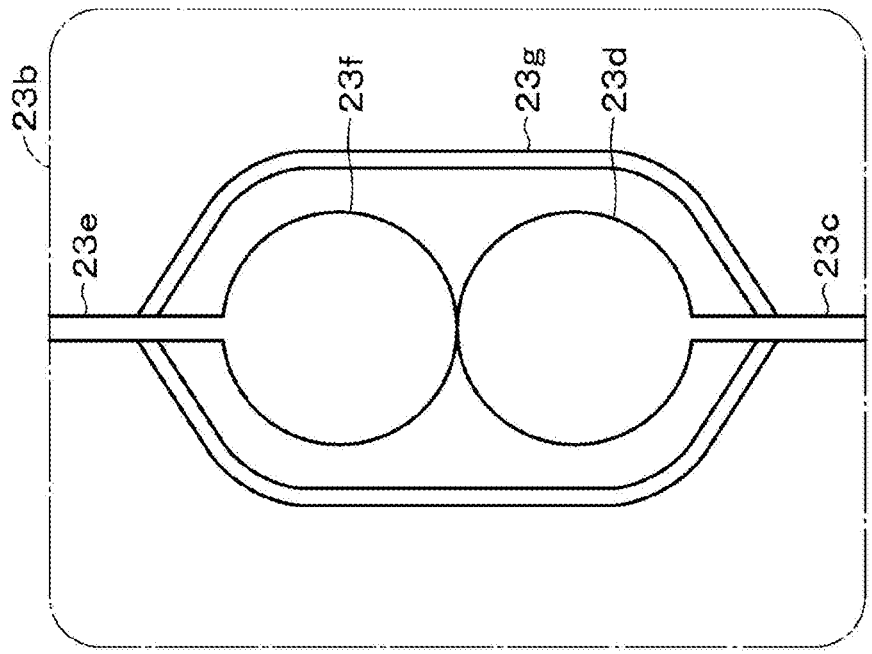
FIG. 5B is an enlarged view illustrating a part of FIG. 5A.
Figure 5A:
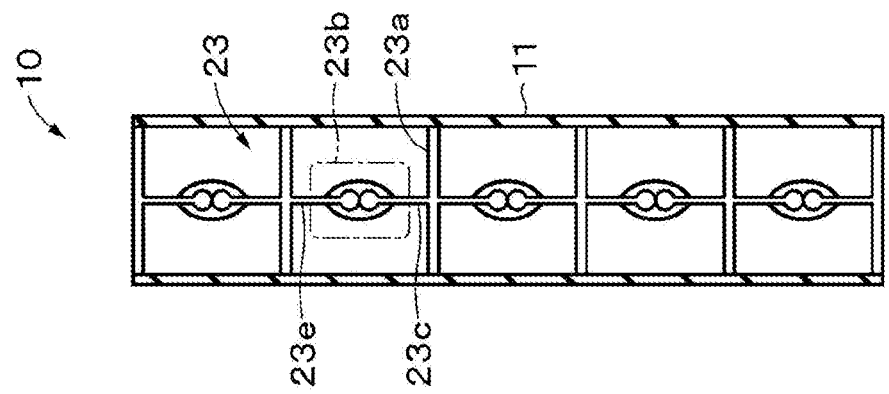
FIG. 5A is a cross-sectional view illustrating a variation of a supporting body.

As illustrated in FIGS. 5A and 5B, the actuator 10 may be provided with a connected body 23 including a plurality of disk-shaped supporting units 23a and a plurality of joint mechanisms 23b imitating a joint structure of a human body in place of the coil spring 12. The plurality of joint mechanisms 23b connects adjacent supporting units 23a so as to be rotatable in an arbitrary direction. The plurality of supporting units 23a is provided so as to be spaced apart from each other by a predetermined distance and supports the inner peripheral surface of the actuator element 11 discretely in the height direction of the actuator element 11. A shaft portion 23c is perpendicularly erected at the center of one surface of the supporting unit 23a, and a spherical portion (so-called ball stud) 23d is provided at a tip end thereof. On the other hand, a shaft portion 23e is also perpendicularly erected at the center of the other surface of the supporting unit 23a, and a spherical portion (so-called ball stud) 23f is provided at a tip end thereof. The spherical portions 23d and 23f abut each other so as to be rotatable in an arbitrary direction. By adopting a configuration in which the spherical portions 23d and 23f abut in this manner, friction during rotation may be reduced. Furthermore, the abutted spherical portions 23d and 23f are covered with a membrane 23g. By covering the spherical portions 23d and 23f with the membrane 23g in this manner, it is possible to suppress displacement between the abutted spherical portions 23d and 23f. An inner side of the membrane 23g may be filled with liquid, a gel and the like. The spherical portions 23d and 23f and the membrane 23g form the joint mechanism 23b. The openings at both ends of the actuator element 11 are closed by the supporting units 23a.

Figure 6B:
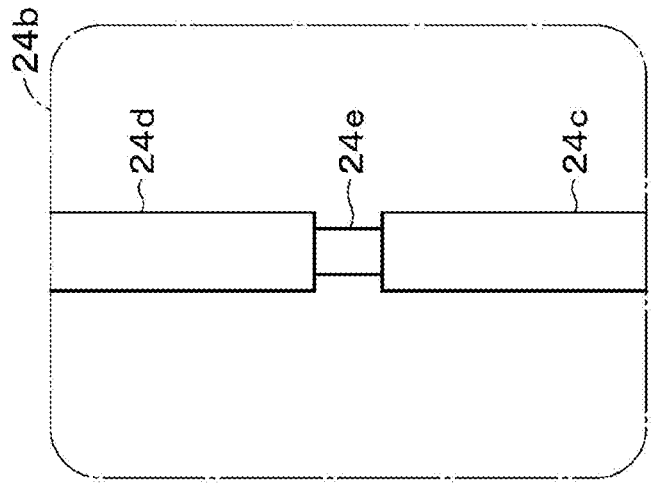
FIG. 6B is an enlarged view illustrating a part of FIG. 6A.
Figure 6A:
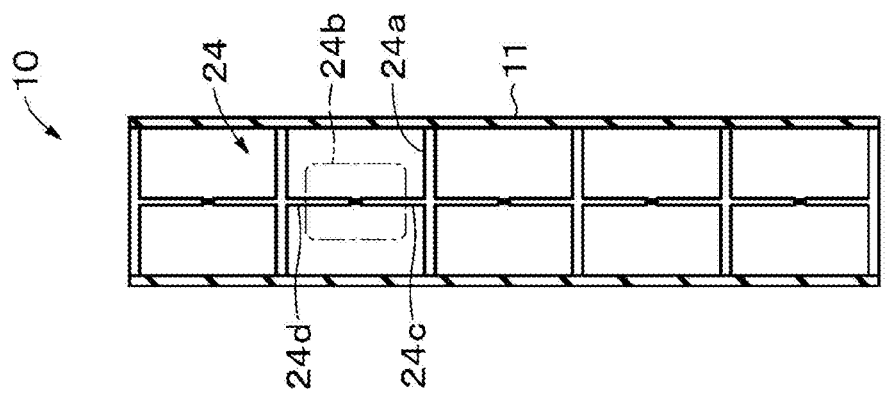
FIG. 6A is a cross-sectional view illustrating a variation of a supporting body.

As illustrated in FIGS. 6A and 6B, the actuator 10 may be provided with a connected body 24 including a plurality of disk-shaped supporting units 24a and a plurality of joint mechanisms 24b imitating a joint structure of insects in place of the coil spring 12. The joint mechanism 24b connects adjacent supporting units 24a so as to be rotatable in an arbitrary direction. The plurality of supporting units 24a is provided so as to be spaced apart from each other by a predetermined distance and supports the inner peripheral surface of the actuator element 11 discretely in the height direction of the actuator element 11. A shaft portion 24c is perpendicularly erected at the center of one surface of the supporting unit 24a, and a shaft portion 24d is perpendicularly erected also at the center of the other surface of the supporting unit 24a. Tip ends of the shaft portions 24c and 24d are separated by a predetermined distance, and the tip ends of the shaft portions 24c and 24d are connected by an elastic body 24e. Therefore, the shaft portions 24c and 24d are rotatable in an arbitrary direction. The elastic body 24e is of a material of low rigidity (material of high flexibility) such as an elastomer, a cushion material, or a spring. The shaft portions 24c and 24d and the elastic body 24e form the joint mechanism 24b. The openings at both ends of the actuator element 11 are closed by the supporting units 24a.

Figure 7B:
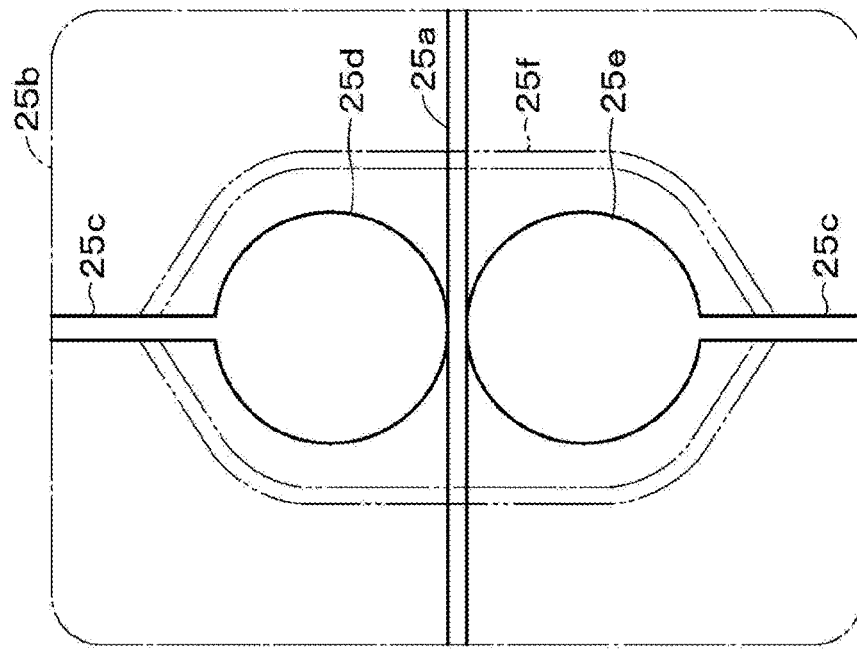
FIG. 7B is an enlarged view illustrating a part of FIG. 7A.
Figure 7A:
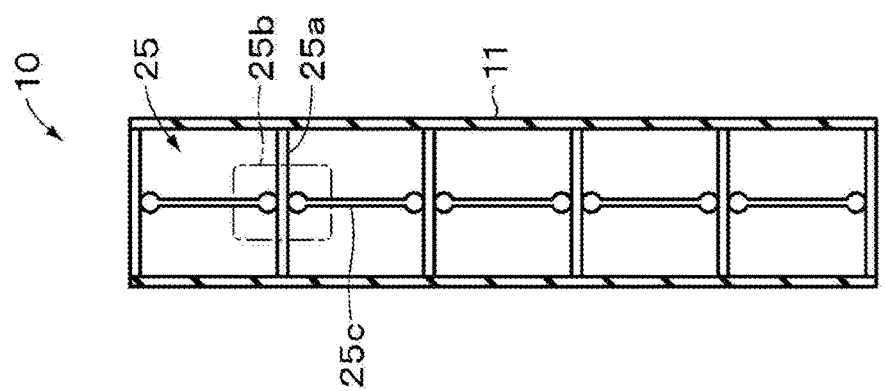
FIG. 7A is a cross-sectional view illustrating a variation of a supporting body.

As illustrated in FIGS. 7A and 7B, the actuator 10 may be provided with a connected body 25 including a plurality of disk-shaped supporting units 25a and a plurality of joint mechanisms 25b imitating a joint structure of a human body in place of the coil spring 12. The plurality of joint mechanisms 25b connects adjacent supporting units 25a so as to be rotatable in an arbitrary direction. The plurality of supporting units 25a is provided so as to be spaced apart from each other by a predetermined distance and supports the inner peripheral surface of the actuator element 11 discretely in the height direction of the actuator element 11. Between the adjacent supporting units 25a, a bar-shaped shaft portion 25c having a spherical portion 25d at one end and a spherical portion 25e at the other end is provided. The shaft portion 25c is a magnet in which a side on the spherical portion 25d is a north pole and a side of the spherical portion 25e is a south pole. The spherical portion 25d is located at the center of one surface of the supporting unit 25a and the spherical portion 25e is located at the center of the other surface of the supporting unit 25a. The spherical portions 25e and 25d having different polarities attract each other across the supporting unit 25a. Therefore, the shaft portion 25c adjacent across the supporting unit 25a may rotate in an arbitrary direction. The spherical portions 25e and 25d may be covered with a membrane 25f, but unlike the joint mechanism 23b illustrated in FIG. 5, in the joint mechanism 25b, the spherical portions 25e and 25d attract by a magnetic force, so that it is not required that the spherical portions 25e are 25d are covered with the membrane 25f. The openings at both ends of the actuator element 11 are closed by the supporting units 25a.

Figure 8:
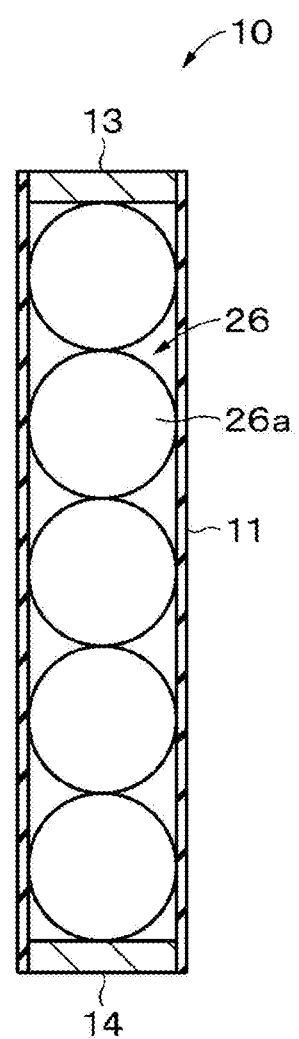
FIG. 8 is a cross-sectional view illustrating a variation of a supporting body.

As illustrated in FIG. 8, the actuator 10 may also be provided with a supporting body 26 including a plurality of spherical bodies 26a accommodated in the tubular actuator element 11 in place of the coil spring 12. The plurality of spherical bodies 26a is accommodated in the actuator element 11 such that the spherical bodies 26a adjacent to each other in the height direction of the actuator element 11 come into contact with each other. As a result, the inner peripheral surface of the actuator element 11 is supported discretely in the height direction of the actuator element 11 by the plurality of spherical bodies 26a, and the actuator 10 is rotatable in an arbitrary direction.

The actuator 10 may be provided with a supporting body including a polymer resin capable of supporting the inner peripheral surface of the actuator element 11 discretely in the height direction of the actuator element 11 in place of the coil spring 12. As a specific example of the polymer resin, for example, there may be an insulating elastomer similar to that of the dielectric layer 11a.

Figure 9:
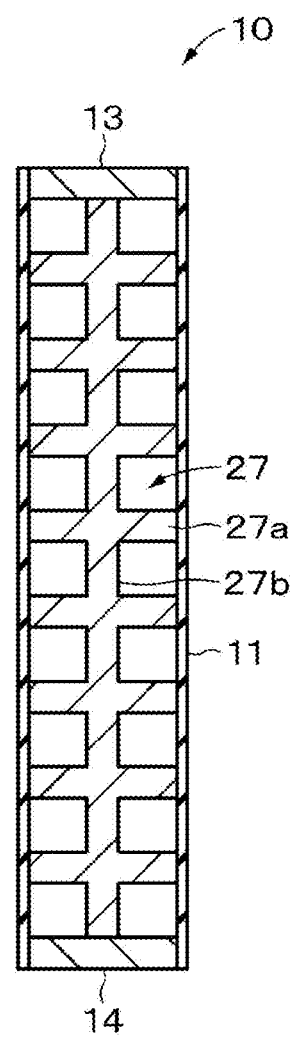
FIG. 9 is a cross-sectional view illustrating a variation of a supporting body.

As illustrated in FIG. 9, a supporting body 27 including a polymer resin may include a plurality of supporting units 27a and a plurality of shaft portions 27b. The supporting unit 27a and the shaft portion 27b are integrally molded of the polymer resin. The supporting unit 27a has a disk shape and supports the inner peripheral surface of the actuator element 11 by an outer peripheral portion thereof. The shaft portion 27b connects the supporting units 27a adjacent to each other in the height direction of the actuator element 11. The sealing members 13 and 14 and the supporting body 27 may be integrally molded of the polymer resin.

(Variation of Method of Manufacturing Actuator)

Figure 10A:
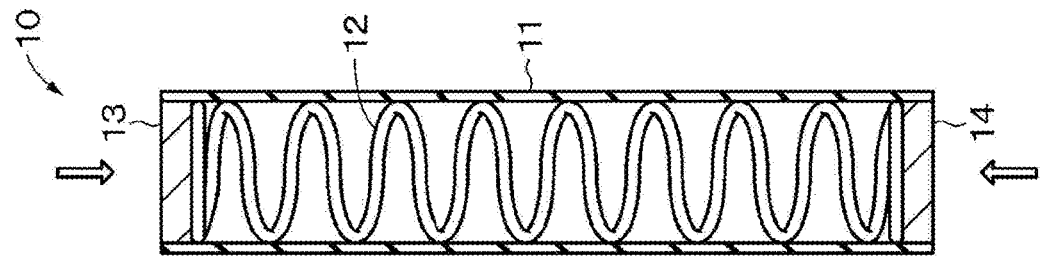
FIGS. 10A and 10B are flowcharts for illustrating a variation of a method of manufacturing an actuator.
Figure 10B:
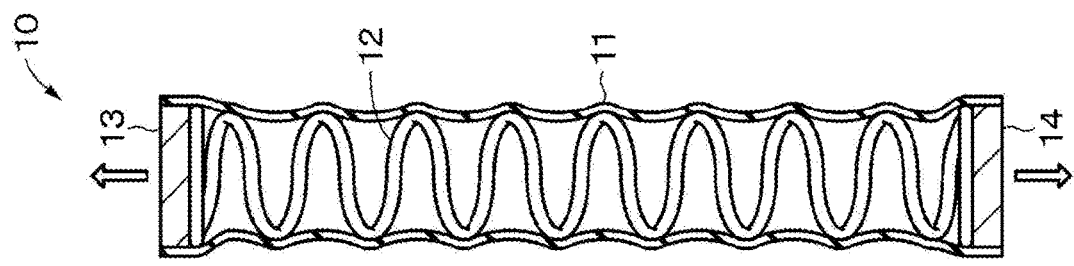

The actuator 10 may also be manufactured in the following manner. First, as illustrated in FIG. 10A, the actuator 10 is assembled in a state in which the coil spring 12 is stretched. At that time, a volume of the internal space of the actuator 10 is larger than the volume of the internal space of the actuator 10 finally obtained, and the constriction occurs on the side surface of the actuator element 11. Next, as illustrated in FIG. 10B, the stretch of the coil spring 12 is released to reduce the volume of the internal space of the actuator 10, thereby increasing the internal pressure of the actuator 10. As a result, an intended actuator 10 in which the constriction on the peripheral surface of the actuator element 11 is suppressed is obtained.

Note that it is also possible to increase the internal pressure of the actuator 10 by reducing the volume of the internal space of the actuator 10 by pressurizing one or both ends of the actuator 10 to decrease a height of the actuator 10 after assembling the actuator 10 in a state in which the coil spring 12 is not stretched.

(Other Variations)

The actuator element 11 may also include stacked sheets of dielectric elastomer actuator elements. In this case, a plurality of dielectric elastomer actuator elements formed in advance into a cylindrical shape may be concentrically stacked around the coil spring 12, or a single dielectric elastomer actuator element having a band shape may be wound around the coil spring 12 to stacked. As described in the first embodiment, the occurrence of the constriction on the peripheral surface of the actuator element 11 is suppressed, so that it is possible to suppress entry of air between the stacked dielectric elastomer actuator elements in a case where the dielectric elastomer actuator elements are stacked.

The actuator 10 may also be provided with first and second electrodes provided on entire or substantially entire both surfaces of the dielectric layer 11a in place of the electrodes 11a and 11b.

In the first embodiment, the configuration in which the actuator element 11 and the coil spring 12 have the cylindrical shape is described as an example; however, the actuator element 11 and the coil spring 12 may have a rectangular tubular shape such as a square tubular shape.

The internal space of the actuator 10 may be filled with liquid or a solid in place of gas. Here, the liquid is, for example, water, saline solution, or the like. Furthermore, the solid is, for example, a sol, a gel, or the like.

2 Second Embodiment

[Configuration of Endoscope Module]

Figure 11:
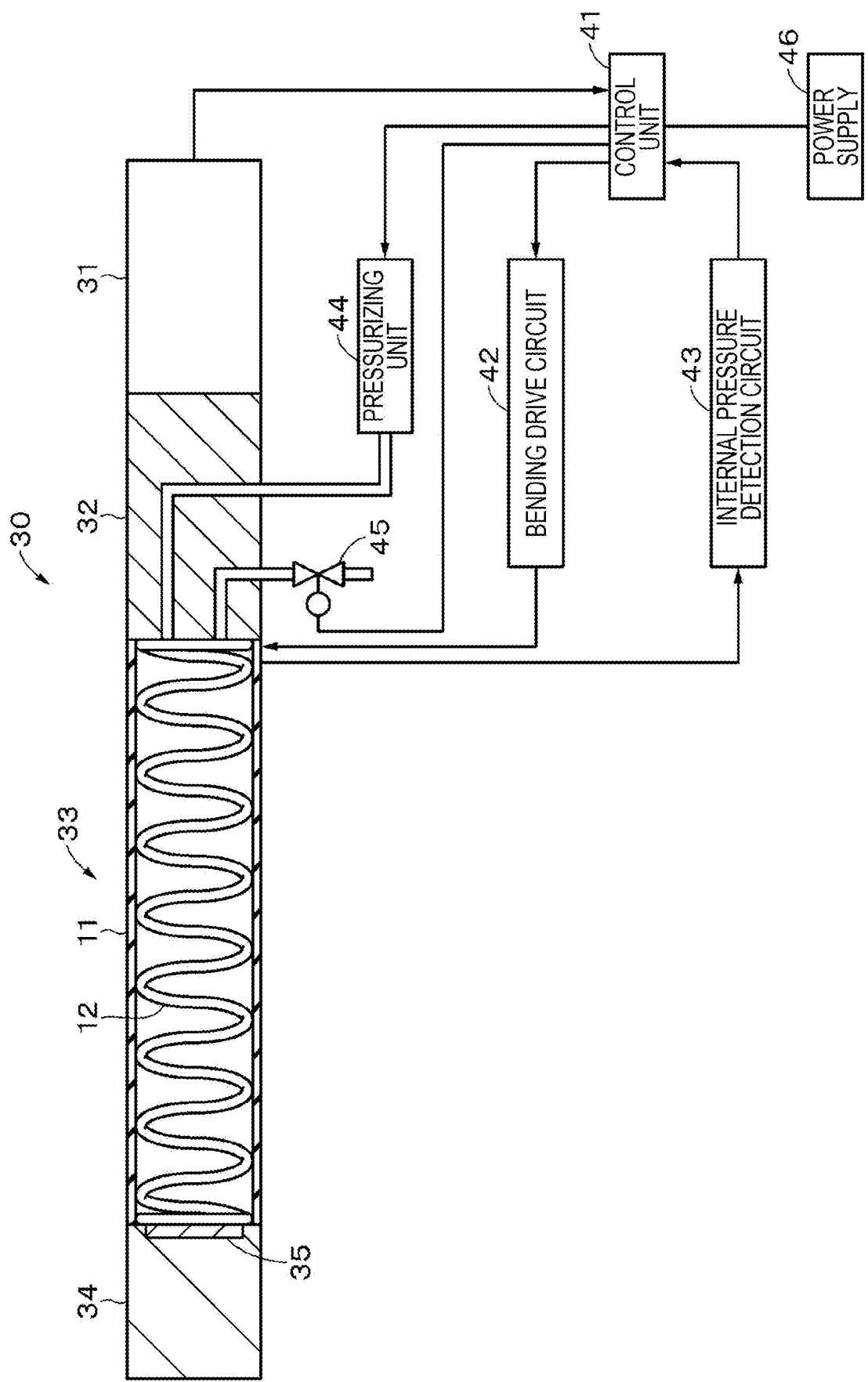
FIG. 11 is a cross-sectional view illustrating a configuration of an endoscope module according to a second embodiment of the present technology.

As illustrated in FIG. 11, an endoscope module according to a second embodiment of the present technology is provided with an endoscope 30, a control unit 41, a bending drive circuit 42, an internal pressure detection circuit 43, a pressurizing unit 44, and a depressurizing unit 45. The control unit 41 is connected to a power supply 46. Note that, in the second embodiment, a portion similar to that in the first embodiment is assigned with the same reference sign and the description thereof is omitted.

The endoscope 30 is provided with an operating unit 31, a supporting unit 32, an actuator 33 being a bending unit, a tip end 34, and a pressure-sensitive sensor 35. The actuator 33, the pressure-sensitive sensor 35, the control unit 41, the bending drive circuit 42, the internal pressure detection circuit 43, the pressurizing unit 44, and the depressurizing unit 45 form an actuator module. The pressure-sensitive sensor 35 and the internal pressure detection circuit 43 form a detecting unit which detects a pressure in an internal space of the actuator 33.

The operating unit 31 is provided with a button, a knob, and the like for operating the endoscope. The supporting unit 32 is provided between the operating unit 31 and the actuator 33 to support the actuator 33. The supporting unit 32 has rigidity and is provided with a vent hole therein which connects the pressurizing unit 44 and the actuator 33.

Figure 12:
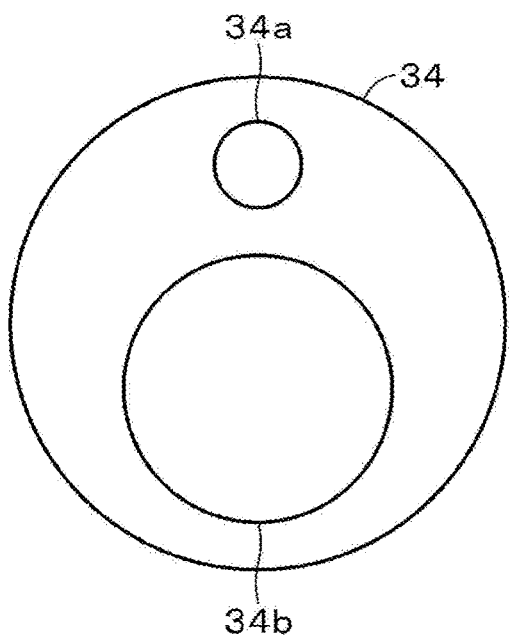
FIG. 12 is a plan view illustrating a configuration of a tip end.

The actuator 33 is provided with an actuator element 11 and a coil spring 12, and the internal space of the actuator 33 is sealed. One opening of the actuator element 11 is closed by the tip end 34 and an opening at the other end is closed by the supporting unit 32. As illustrated in FIG. 12, an illumination lens 34a and an objective lens 34b are provided on a tip end surface of the tip end 34. A portion of the illumination lens 34a and the objective lens 34b on the surface of the tip end 34 is of, for example, stainless steel or the like. The illumination lens 34a and the objective lens 34b are, for example, glass lenses. An illumination device is provided inside the illumination lens 34a, and an imaging element such as a charge coupled device (CCD) or a complementary metal oxide semiconductor (CMOS) is provided inside the objective lens 34*b*. The imaging element is connected to a display device not illustrated via an image processing unit not illustrated.

The tip end 34 and the operating unit 31 are connected to each other by a cable arranged in the internal space of the actuator 33, and an operation signal is supplied from the operating unit 31 to the tip end 34 via this cable. Furthermore, the tip end 34 and the image processing unit are connected by a cable arranged in the internal space of the actuator 33, and a video signal is supplied from the tip end 34 to the image processing unit via this cable. However, the operating unit 31 may wirelessly supply the operation signal to the tip end 34, or the tip end 34 may wirelessly supply the video signal to the image processing unit.

The pressure-sensitive sensor 35 is arranged in a portion to close the opening on one end of the actuator element 11 out of the tip end 34. However, an arrangement position of the pressure-sensitive sensor 35 is not limited to there as long as this is a position where the sensor may detect the internal pressure of the actuator 33. The pressure-sensitive sensor 35 outputs an electric signal corresponding to the internal pressure of the actuator 33 to the internal pressure detection circuit 43. As the pressure-sensitive sensor 35, for example, a diaphragm gauge or the like may be used.

The internal pressure detection circuit 43 detects the internal pressure of the actuator 33 on the basis of the electric signal supplied from the pressure-sensitive sensor 35 and supplies the same to the control unit 41. The pressurizing unit 44 is a pump, a regulator or the like, and supplies gas to the internal space of the actuator 33 under the control of the control unit 41 to pressurize the internal space of the actuator 33. The gas is at least one type of air, a rare gas, carbon dioxide and the like, for example. The depressurizing unit 45 is a solenoid valve such as a diaphragm valve and discharges the gas in the internal space of the actuator 33 to decrease the pressure in the internal space of the actuator 33 under the control of the control unit 41.

The control unit 41 controls the bending drive circuit 42 and the pressurizing unit 44 on the basis of the control signal supplied from the operating unit 31. On the basis of the internal pressure supplied from the internal pressure detection circuit 43, the control unit 41 feedback-controls the pressurizing unit 44 and the depressurizing unit 45 such that the internal pressure of the actuator 33 becomes a prescribed pressure. Here, the prescribed pressure is a pressure at which occurrence of constriction of the actuator 33 is suppressed. Note that, when the internal pressure of the actuator 33 is too high, there is a possibility that swelling might occur in the actuator element 11, so that an upper limit value of the internal pressure of the actuator 33 is preferably a pressure at which the swelling of the actuator element 11 does not occur. The bending drive circuit 42 drives the actuator 33 to bend on the basis of the control signal supplied from the control unit 41.

[Method of Controlling Internal Pressure at Power On]

Figure 13:
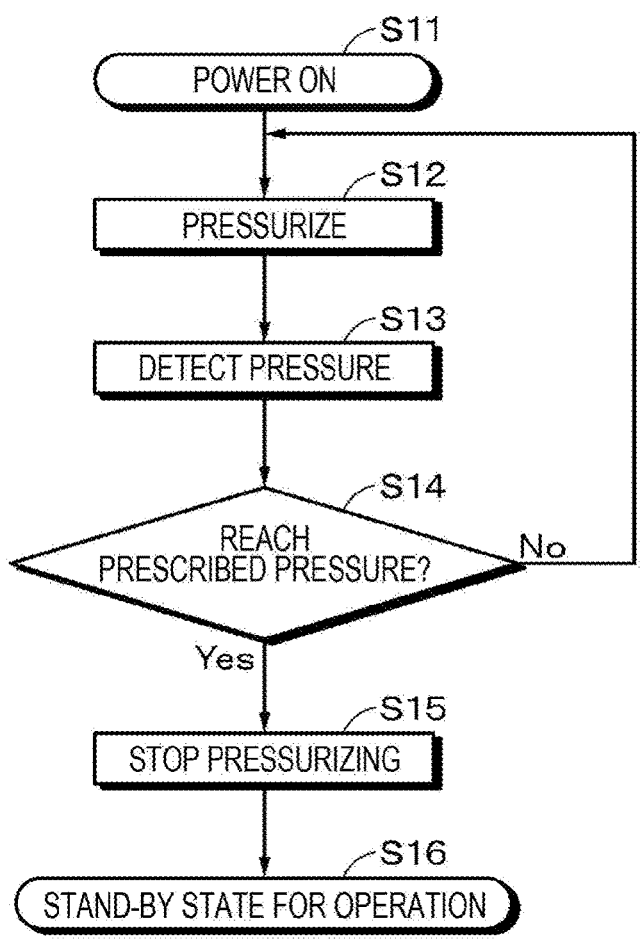

Next, with reference to FIG. 13, a method of controlling the internal pressure at power on described. First, when the power supply 46 is put on at step S11, the control unit 41 drives the pressurizing unit 44 at step S12 to pressurize the actuator 33, thereby increasing the internal pressure of the actuator 33. Next, at step S13, the internal pressure detection circuit 43 detects the internal pressure of the actuator 33 on the basis of the electric signal supplied from the pressure-sensitive sensor 35, and supplies a detection result to the control unit 41.

Next, at step S14, the control unit 41 determines whether or not the internal pressure of the actuator 33 reaches the prescribed pressure on the basis of the internal pressure supplied from the internal pressure detection circuit 43. In a case where it is determined at step S14 that the internal pressure of the actuator 33 reaches the prescribed pressure, the control unit 41 stops the pressurizing unit 44 at step S15, and at step S16, the control unit 41 is put into a stand-by state for operation on the endoscope 30. On the other hand, in a case where it is determined at step S14 that the internal pressure of the actuator 33 does not reach the prescribed pressure, the control unit 41 returns the process to step S12.

[Method of Controlling Internal Pressure at Operation Time]

Figure 14:
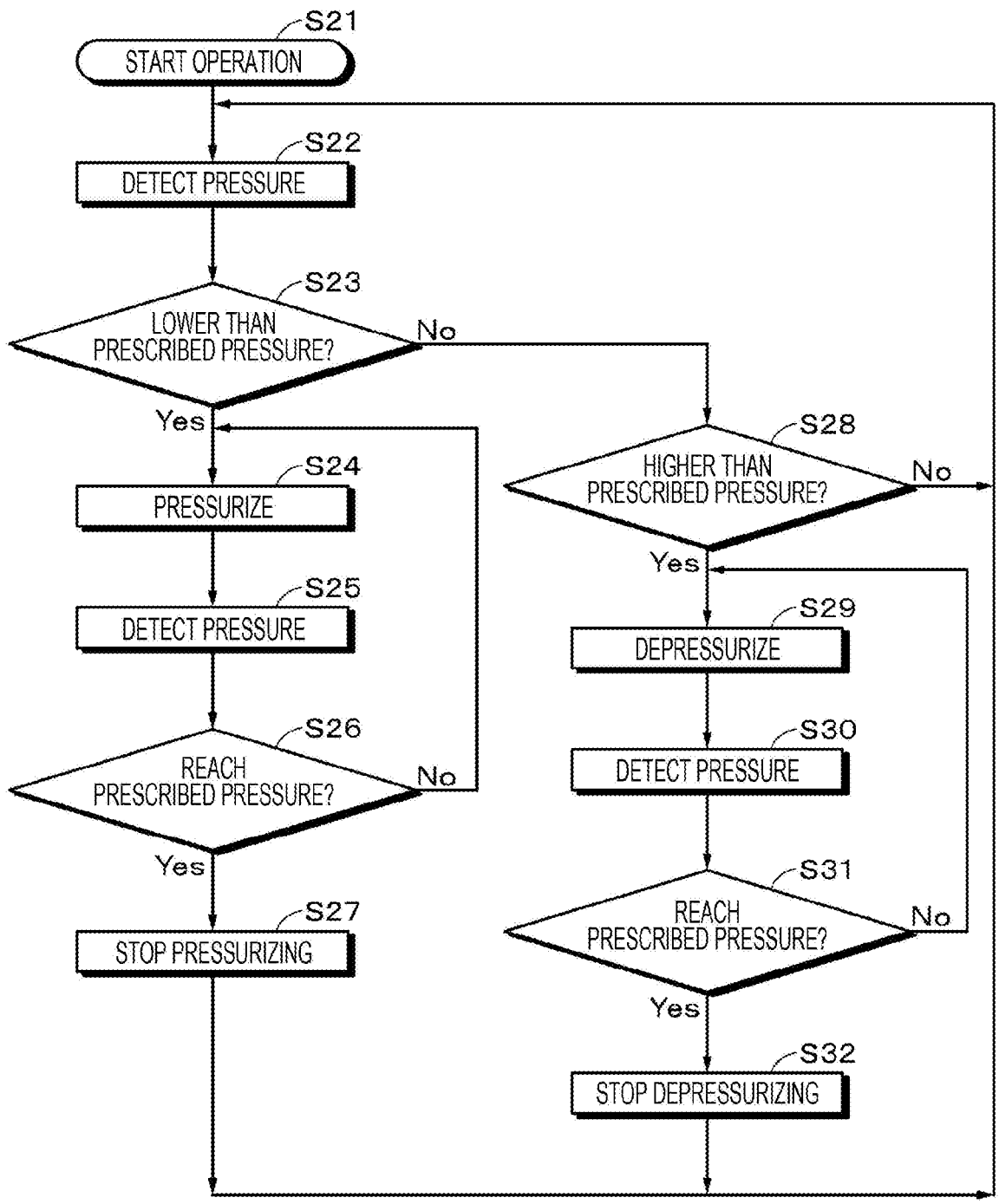
FIG. 14 is a flowchart for illustrating a method of controlling an internal pressure at the time of operation.

Next, with reference to FIG. 14, a method of controlling the internal pressure at the time of operation is described. First, when the operation of the endoscope 30 is started at step S21, the internal pressure detection circuit 43 detects the internal pressure of the actuator 33 on the basis of the electric signal supplied from the pressure-sensitive sensor 35 at step S22, and supplies a detection result to the control unit 41. Next, at step S23, the control unit 41 determines whether or not the internal pressure of the actuator 33 is lower than the prescribed pressure on the basis of the internal pressure supplied from the internal pressure detection circuit 43.

In a case where it is determined at step S23 that the internal pressure of the actuator 33 is lower than the prescribed pressure, at step S24, the control unit 41 drives the pressurizing unit 44 to pressurize the interior of the actuator 33, thereby increasing the internal pressure of the actuator 33. Next, at step S25 the internal pressure detection circuit 43 detects the internal pressure of the actuator 33 on the basis of the electric signal supplied from the pressure-sensitive sensor 35, and supplies a detection result to the control unit 41.

Next, at step S26, the control unit 41 determines whether or not the internal pressure of the actuator 33 reaches the prescribed pressure on the basis of the internal pressure supplied from the internal pressure detection circuit 43. In a case where it is determined at step S26 that the internal pressure of the actuator 33 reaches the prescribed pressure, at step S27, the control unit 41 stops the pressurizing unit 44 and returns the procedure to step S22. On the other hand, in a case where it is determined at step S26 that the internal pressure of the actuator 33 does not reach the prescribed pressure, the control unit 41 returns the process to step S24.

In a case where it is determined at step S23 that the internal pressure of the actuator 33 is not lower than the prescribed pressure, at step S28, the control unit 41 determines whether or not the internal pressure of the actuator 33 is higher than the prescribed pressure on the basis of the internal pressure supplied from the internal pressure detection circuit 43. In a case where it is determined at step S28 that the internal pressure of the actuator 33 is higher than the prescribed pressure, at step S29, the control unit 41 drives the depressurizing unit 45 to depressurize the interior of the actuator 33, thereby decreasing the internal pressure of the actuator 33. On the other hand, in a case where it is determined at step S28 that the internal pressure of the actuator 33 is not higher than the prescribed pressure, the control unit 41 returns the procedure to step S22.

Next, at step S30, the internal pressure detection circuit 43 detects the internal pressure of the actuator 33 on the basis of the electric signal supplied from the pressure-sensitive sensor 35, and supplies a detection result to the control unit 41. Next, at step S31, the control unit 41 determines whether or not the internal pressure of the actuator 33 reaches the prescribed pressure on the basis of the internal pressure supplied from the internal pressure detection circuit 43. In a case where it is determined at step S31 that the internal pressure of the actuator 33 reaches the prescribed pressure, at step S32, the control unit 41 stops the depressurizing unit 45 and returns the procedure to step S22. On the other hand, in a case where it is determined at step S31 that the internal pressure of the actuator 33 does not reach the prescribed pressure, the control unit 41 returns the process to step S29.

[Effect]

Since the endoscope module according to the second embodiment is provided with the pressurizing unit 44 for increasing the internal pressure of the actuator 33, the internal pressure of the actuator 33 may be made higher than the external pressure of the actuator 33. Therefore, an effect similar to that of the first embodiment may be obtained.

Furthermore, since the pressurizing unit 44 for increasing the internal pressure of the actuator 33 and the depressurizing unit 45 for decreasing the internal pressure of the actuator 33 are provided, the internal pressure of the actuator 33 may be adjusted to the prescribed pressure at the time of the operation of the endoscope module.

[Variation]

Figure 15:
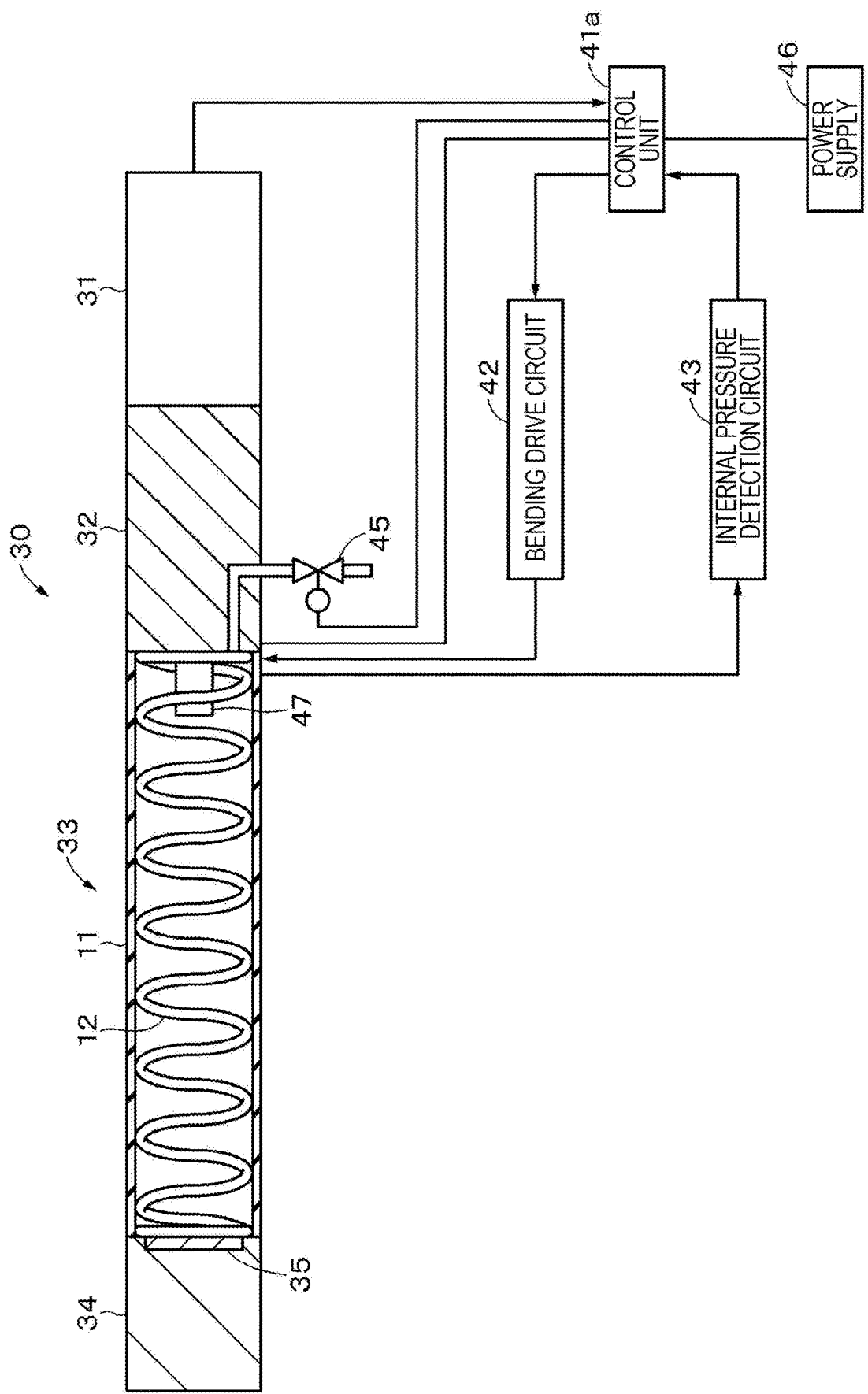
FIG. 15 is a cross-sectional view illustrating a configuration of an endoscope module according to a variation of a second embodiment of the present technology.

As illustrated in FIG. 15, the endoscope module may also be provided with a heating unit 47 in place of the pressurizing unit 44. As the heating unit 47, for example, an infrared heater or the like may be used. The control unit 41a controls the heating unit 47 to heat the internal space of the actuator 33 to expand the gas, thereby increasing the internal pressure of the actuator 33.

The endoscope module may also be provided with both the pressurizing unit 44 and the heating unit 47. In this case, both the pressurizing unit 44 and the heating unit 47 may be operated at the same time, or the pressurizing unit 44 and the heating unit 47 may be selectively operated by mode switching.

The endoscope module is not required to be provided with the depressurizing unit 45. In this case, the control unit 41 executes only the operation of increasing the internal pressure of the actuator 33 in a flowchart illustrated in FIG. 14.

Pressure detecting operations at steps S22, S25, and S30 illustrated in FIG. 14 may be repeatedly performed at predetermined time intervals when the endoscope module is operated.

3 Third Embodiment

[Configuration of Endoscope Module]

Figure 16:
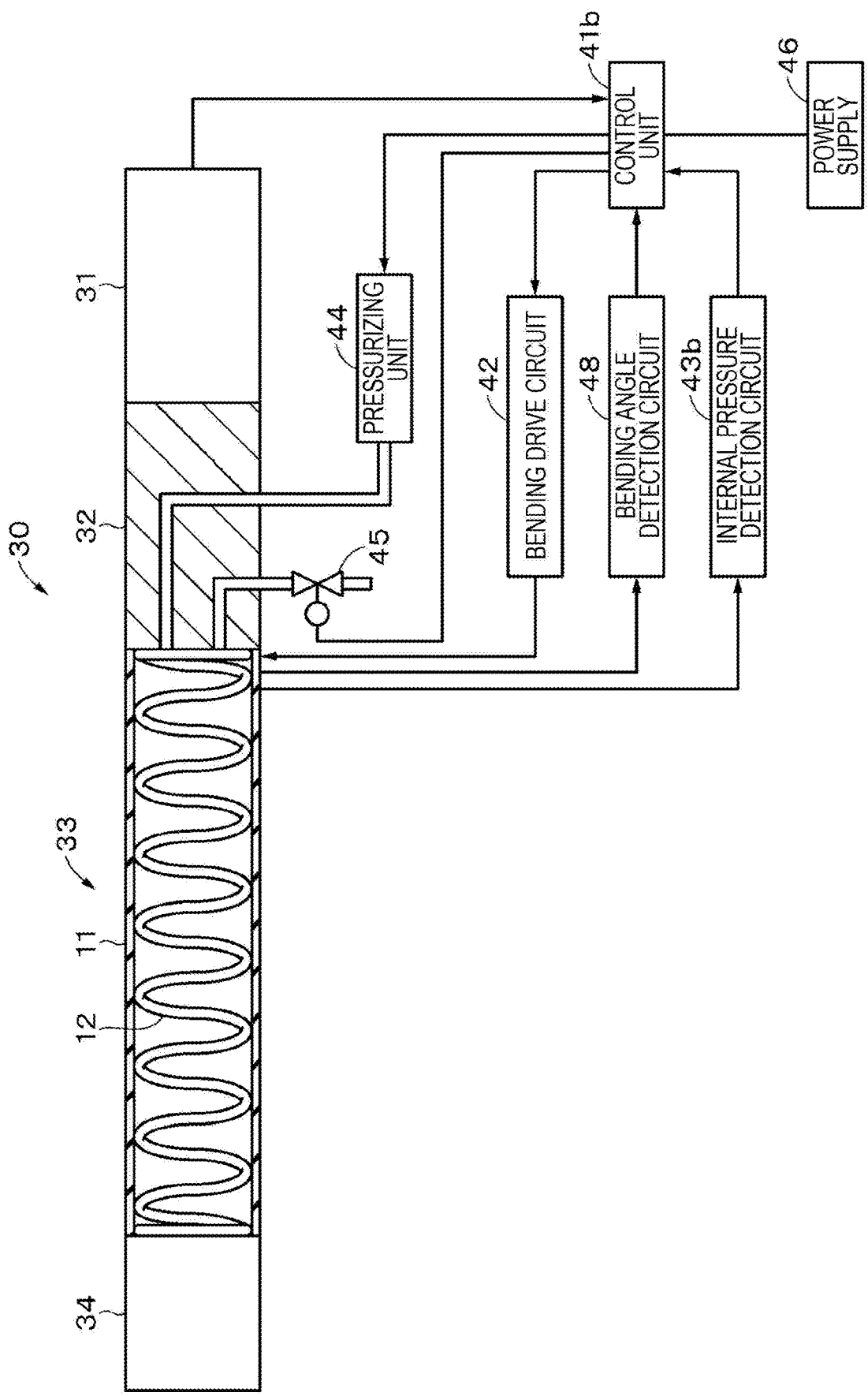
FIG. 16 is a cross-sectional view illustrating a configuration of an endoscope module according to a third embodiment of the present technology.

As illustrated in FIG. 16, an endoscope module according to a third embodiment of the present technology is provided with an endoscope 30, a control unit 41b, a bending drive circuit 42, a bending angle detection circuit 48, an internal pressure detection circuit 43b, a pressurizing unit 44, and a depressurizing unit 45. The control unit 41b is connected to a power supply 46. Note that, in the third embodiment, a portion similar to that in the second embodiment is assigned with the same reference sign and the description thereof is omitted.

Electrodes 11b and 11c (refer to FIGS. 2A and 2B) provided on an inner peripheral surface and an outer peripheral surface, respectively, of a dielectric layer 11a included in an actuator element 11 are deformed by bending or a change in internal pressure of the actuator 33. The internal pressure detection circuit 43b detects the internal pressure of the actuator 33 from a change in electrostatic capacitance (change in distance) between the electrodes 11b and 11c opposed to each other with the dielectric layer 11a interposed therebetween and supplies a detection result to the control unit 41b. The bending angle detection circuit 48 detects a bending angle of the actuator 33 from a change in electric resistance caused by the deformation of the electrodes 11b and 11c and supplies a detection result to the control unit 41b. On the basis of the internal pressure supplied from the internal pressure detection circuit 43b and the bending angle supplied from the bending angle detection circuit 48, the control unit 41b feedback-controls the pressurizing unit 44 and the depressurizing unit 45 such that the internal pressure of the actuator 33 becomes a prescribed pressure.

[Effect]

The endoscope module according to the third embodiment feedback-controls the pressurizing unit 44 and the depressurizing unit 45 such that the internal pressure of the actuator 33 becomes the prescribed pressure on the basis of the internal pressure and the bending angle of the actuator 33. Therefore, it is possible to appropriately control the internal pressure of the actuator 33 when operating the actuator 33 as compared with the endoscope module according to the second embodiment.

[Variation]

The endoscope module may be provided with a heating unit 47 in place of the pressurizing unit 44 or may be provided with the heating unit 47 together with the pressurizing unit 44. Furthermore, the endoscope module is not required to be provided with the depressurizing unit 45.

4 Fourth Embodiment

[Configuration of Actuator]

Figure 17:
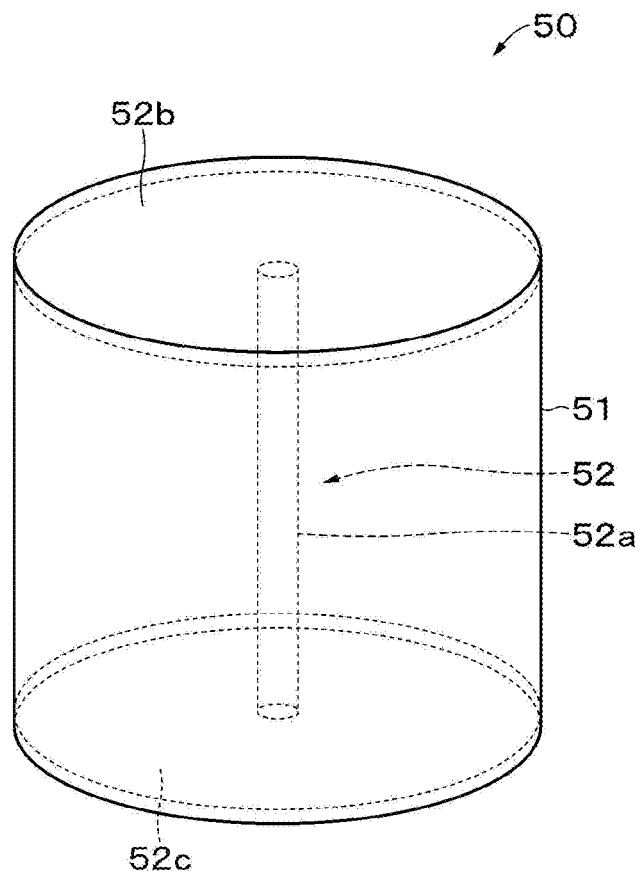
FIG. 17 is a perspective view illustrating a configuration of an actuator according to a fourth embodiment of the present technology.

An actuator 50 according to a fourth embodiment of the present technology is a speaker having a sealed structure and is provided with a cylindrical actuator element 51 and a supporting body 52 which supports both ends of the actuator element 11 as illustrated in FIG. 17. An internal pressure of the actuator 50 is higher than an external pressure of the actuator 50.

The cylindrical actuator element 51 is provided with a cylindrical dielectric layer, a first electrode provided on an inner peripheral surface of the dielectric layer, and a second electrode provided on an outer peripheral surface of the dielectric layer. The first and second electrodes may be provided on the inner peripheral surface and the outer peripheral surface, respectively, of the dielectric layer in a predetermined pattern or provided on entire or substantially entire inner peripheral surface and outer peripheral surface, respectively, of the dielectric layer. The supporting body 52 is provided with a shaft portion 52a and disk-shaped supporting units 52b and 52c provided at both ends of the shaft portion 52a.

[Effect]

In the actuator 50 according to the fourth embodiment, since the internal pressure of the actuator 50 is higher than the external pressure of the actuator 50, an effect similar to that of the actuator 10 according to the first embodiment may be obtained.

[Variation]

The actuator element 11 may have a rectangular tubular shape such as a square tubular shape and the supporting units 52b and 52c may have a polygonal shape such as a square shape.

The actuator 50 in the fourth embodiment, the pressure-sensitive sensor 35, the control unit 41, the internal pressure detection circuit 43, the pressurizing unit 44, and the depressurizing unit 45 in the second embodiment may form the actuator module. In this case, the actuator module may be provided with a heating unit 47 in place of the pressurizing unit 44, or may be provided with the heating unit 47 together with the pressurizing unit 44. Furthermore, the actuator module is not required to be provided with the depressurizing unit 45.

5 Fifth Embodiment

[Configuration of Actuator]

Figure 18:
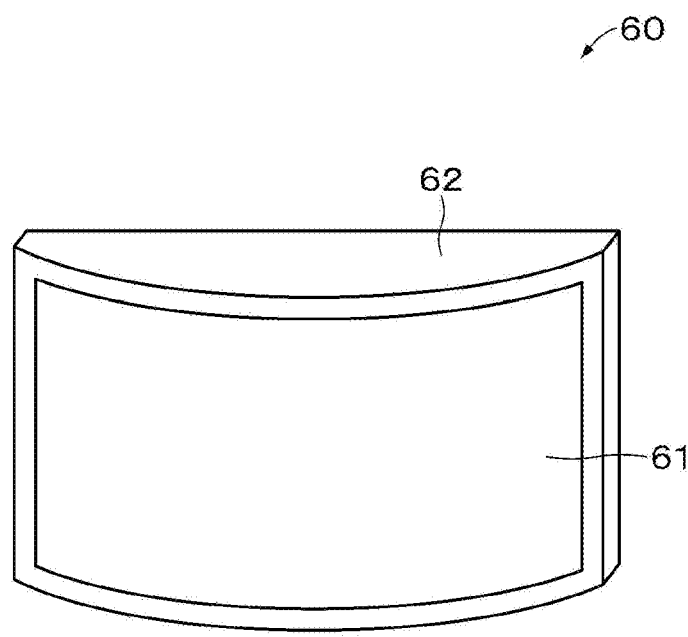
FIG. 18 is a perspective view illustrating a configuration of an actuator according to a variation of a fifth embodiment of the present technology.

An actuator 60 according to a fifth embodiment of the present technology is a speaker having a sealed structure and is provided with a rectangular actuator element 61 and a supporting body 62 which supports a peripheral edge of the actuator element 61 as illustrated in FIG. 18. An internal pressure of the actuator 60 is higher than an external pressure of the actuator 60.

The rectangular actuator element 61 is provided with a rectangular dielectric layer, a first electrode provided on one surface of the dielectric layer, and a second electrode provided on the other surface of the dielectric layer. The first and second electrodes may be provided on both surfaces of the dielectric layer in a predetermined pattern or may be provided on entire or substantially entire both surfaces of the dielectric layer. The supporting body 62 supports the actuator element 61 in a convexly curved state.

[Effect]

In the actuator 60 according to the fifth embodiment, since the internal pressure of the actuator 60 is higher than the external pressure of the actuator 60, an effect similar to that of the actuator 10 according to the first embodiment may be obtained.

[Variation]

The actuator 60 may form the actuator module in a manner similar to that of the variation of the fourth embodiment.

Although the embodiments of the present technology are heretofore described specifically, the present technology is not limited to the above-described embodiments, and various modifications based on the technical idea of the present technology may be made.

For example, the configuration, the method, the step, the shape, the material, the numerical value and the like described in the above-described embodiments are merely examples, and the configuration, the method, the step, the shape, the material, the numerical value and the like different from those may also be used as necessary.

Furthermore, the configuration, the method, the step, the shape, the material, the numerical value and the like of the above-described embodiments may be combined with each other without departing from the gist of the present technology.

Furthermore, the present technology may also adopt the following configurations.

(1)

An actuator provided with:

a tubular actuator element; and a supporting body which supports an inner peripheral surface of the actuator element, in which an internal pressure of the actuator element is higher than an external pressure of the actuator element.

(2)

The actuator according to (1), in which the supporting body supports the inner peripheral surface of the actuator element discretely in a height direction of the actuator element.

(3)

The actuator according to (1) or (2), in which the supporting body is a coil spring, a connected body obtained by connecting a plurality of supporting units by a joint mechanism, or a plurality of spherical bodies.

(4)

The actuator according to any one of (1) to (3), further provided with: gas or liquid filling an internal space of the actuator element.

(5)

The actuator according to any one of (1) to (4), in which the actuator element is a dielectric elastomer actuator element.

(6)

The actuator according to (5), in which the dielectric elastomer actuator element is stacked.

(7)

The actuator according to (5) or (6), in which the actuator element is provided with a tubular dielectric layer, a first electrode provided on an inner peripheral surface of the dielectric layer, and a second electrode provided on an outer peripheral surface of the dielectric layer.

(8)

The actuator according to (5) or (6), in which the actuator element is provided with a tubular dielectric layer, a plurality of first electrodes provided on an inner peripheral surface of the dielectric layer, and a plurality of second electrodes provided on an outer peripheral surface of the dielectric layer, and the first and second electrodes are opposed to each other with the dielectric layer interposed therebetween and extend in a height direction of the actuator element.

(9)

An endoscope provided with:

the actuator according to any one of (1) to (8).

(10)

An actuator module provided with:

an actuator including a tubular actuator element, and a supporting body which supports an inner peripheral surface of the actuator element;

a control unit which controls drive of the actuator; and a pressurizing unit which pressurizes an internal space of the actuator.

(11)

The actuator module according to (10), further provided with:

a detecting unit which detects a pressure in the internal space, in which the control unit controls the pressurizing unit according to a detection result of the detecting unit.

(12)

The actuator module according to (11), further provided with:

a depressurizing unit which depressurizes the internal space, in which the control unit controls the depressurizing unit according to a detection result of the detecting unit.

(13)

The actuator module according to any one of (10) to (12), in which the pressurizing unit pressurizes the internal space of the actuator by supplying gas or liquid to the internal space.

(14)

An endoscope module provided with:

the actuator module according to any one of (10) to (13).

(15)

An actuator provided with:

an actuator element; and a supporting body which supports the actuator element, in which an internal pressure of the actuator element is higher than an external pressure of the actuator element.

(16)

The actuator according to (15), in which the actuator element has a tubular shape, and the supporting body supports both ends of the actuator element.

(17)

The actuator according to (15) or (16), in which the supporting body supports a peripheral edge of the actuator element.

(18)

A controlling method provided with:

detecting a pressure in an internal space of an actuator; and pressurizing or depressurizing the internal space of the actuator on the basis of a result of the detection.

REFERENCE SIGNS LIST 10, 33, 50, 60 Actuator
11, 51, 61 Actuator element 11
12 Coil spring (supporting body)
13, 14 Sealing member
21, 22, 23, 24, 25 Connected body (supporting body)
26, 27, 52, 62 Supporting body
26a Spherical body
35 Pressure-sensitive sensor
41, 41a, 41b Control unit
42 Bending drive circuit
43 Internal pressure detection circuit
44 Pressurizing unit
45 Depressurizing unit

What is claimed is:

1. An actuator comprising:
a tubular actuator element, wherein the tubular actuator element includes a sealed internal space; and
a supporting body which supports an inner peripheral surface of the tubular actuator element,
wherein the supporting body comprises a plurality of supporting units and a plurality of joint mechanisms,
wherein the plurality of joint mechanisms have a spherical shape and connect adjacent supporting units so as to be rotatable in an arbitrary direction, and
wherein the sealed internal space maintains an internal pressure that is higher than an external pressure of the sealed internal space.

2. The actuator according to claim 1,
wherein the supporting body supports the inner peripheral surface of the tubular actuator element discretely in a height direction of the tubular actuator element.

3. The actuator according to claim 1, further comprising:
gas or liquid filling the sealed internal space of the tubular actuator element.

4. The actuator according to claim 1,
wherein the tubular actuator element is a dielectric elastomer actuator element.

5. The actuator according to claim 4,
wherein the dielectric elastomer actuator element is stacked.

6. The actuator according to claim 4,
wherein the tubular actuator element is provided with a tubular dielectric layer, a first electrode provided on an inner peripheral surface of the tubular dielectric layer, and a second electrode provided on an outer peripheral surface of the tubular dielectric layer.

7. The actuator according to claim 4,
wherein the tubular actuator element is provided with a tubular dielectric layer, a plurality of first electrodes provided on an inner peripheral surface of the tubular dielectric layer, and a plurality of second electrodes provided on an outer peripheral surface of the tubular dielectric layer, and
the first and second electrodes are opposed to each other with the tubular dielectric layer interposed therebetween and extend in a height direction of the tubular actuator element.

8. An endoscope comprising:
the actuator according to claim 1.

9. An actuator module comprising:
an actuator including a tubular actuator element, wherein the tubular actuator element includes a sealed internal space;
a supporting body which supports an inner peripheral surface of the tubular actuator element, wherein the supporting body comprises a plurality of supporting units and a plurality of joint mechanisms, and wherein the plurality of joint mechanisms have a spherical shape and connect adjacent supporting units so as to be rotatable in an arbitrary direction;
a control unit which controls drive of the actuator; and
a pressurizing unit which pressurizes the sealed internal space of the actuator.

10. The actuator module according to claim 9, further comprising:
a detecting unit which detects a pressure in the sealed internal space,
wherein the control unit controls the pressurizing unit according to a detection result of the detecting unit.

11. The actuator module according to claim 10, further comprising:
a depressurizing unit which depressurizes the sealed internal space,
wherein the control unit controls the depressurizing unit according to a detection result of the detecting unit.

12. The actuator module according to claim 9,
wherein the pressurizing unit pressurizes the sealed internal space of the actuator by supplying gas or liquid to the sealed internal space.

13. An endoscope module comprising:
the actuator module according to claim 10.

14. An actuator comprising:
an actuator element, wherein the actuator element includes a sealed internal space; and
a supporting body which supports the actuator element, wherein the supporting body comprises a plurality of supporting units and a plurality of joint mechanisms, wherein the plurality of joint mechanisms have a spherical shape and connect adjacent supporting units so as to be rotatable in an arbitrary direction, and
wherein an internal pressure of the sealed internal space is higher than an external pressure of the sealed internal space.

15. The actuator according to claim 14,
wherein the actuator element has a tubular shape, and
the supporting body supports both ends of the actuator element.

16. The actuator according to claim 14,
wherein the supporting body supports a peripheral edge of the actuator element.

17. A controlling method comprising:
- detecting a pressure in a sealed internal space of a tubular actuator element, wherein the tubular actuator element includes a supporting body which supports an inner peripheral surface of the tubular actuator element, wherein the supporting body comprises a plurality of supporting units and a plurality of joint mechanisms, and wherein the plurality of joint mechanisms have a spherical shape and connect adjacent supporting units so as to be rotatable in an arbitrary direction; and
- pressurizing or depressurizing the sealed internal space of the tubular actuator element on a basis of a result of the detection.

* * * * *